United States Patent
Catarino et al.

(10) Patent No.: US 11,712,427 B2
(45) Date of Patent: *Aug. 1, 2023

(54) METHOD FOR INCREASING SERUM ADIPONECTIN FOR TREATMENT AND REDUCTION OF THE RISK OF CARDIOVASCULAR, VASCULAR, AND RELATED DISEASES

(71) Applicant: First Fruits Business Ministry, LLC, Columbia, SC (US)

(72) Inventors: Roger J. Catarino, Columbia, SC (US); William D. Kuhne, Columbia, SC (US)

(73) Assignee: FIRST FRUITS BUSINESS MINISTRY, LLC, Columbia, SC (US)

( * ) Notice: Subject to any disclaimer, the term of this patent is extended or adjusted under 35 U.S.C. 154(b) by 352 days.

This patent is subject to a terminal disclaimer.

(21) Appl. No.: 16/859,710

(22) Filed: Apr. 27, 2020

(65) Prior Publication Data

US 2020/0253910 A1 Aug. 13, 2020

Related U.S. Application Data

(63) Continuation of application No. 16/118,340, filed on Aug. 30, 2018, now Pat. No. 10,632,092.

(60) Provisional application No. 62/552,378, filed on Aug. 30, 2017.

(51) Int. Cl.
*A61K 31/20* (2006.01)
*A61K 47/38* (2006.01)
*A61P 3/04* (2006.01)
*A61K 9/00* (2006.01)
*A61K 9/48* (2006.01)

(52) U.S. Cl.
CPC ............ *A61K 31/20* (2013.01); *A61K 9/0053* (2013.01); *A61K 9/4858* (2013.01); *A61K 47/38* (2013.01); *A61P 3/04* (2018.01)

(58) Field of Classification Search
CPC .... A61K 31/20; A61K 9/0053; A61K 9/4858; A61K 47/38; A61P 3/04
USPC ........................................................ 514/210.2
See application file for complete search history.

(56) References Cited

U.S. PATENT DOCUMENTS

| | | | |
|---|---|---|---|
| 6,054,480 A * | 4/2000 | Cairns ................... | A61K 31/23 514/557 |
| 10,632,092 B2 * | 4/2020 | Catarino ............... | A61K 31/20 |
| 2003/0176328 A1 | 9/2003 | Rasmussen et al. | |
| 2004/0023854 A1 | 2/2004 | Cooper et al. | |
| 2007/0213263 A1 | 9/2007 | Walsh et al. | |
| 2012/0058094 A1 * | 3/2012 | Blaser ...................... | A61P 9/10 435/6.12 |
| 2019/0060267 A1 | 2/2019 | Catarino et al. | |
| 2020/0253910 A1 | 8/2020 | Catarino et al. | |

FOREIGN PATENT DOCUMENTS

WO 2004022596 A1 3/2004

OTHER PUBLICATIONS

Pack et al Mayo Clin Proc. 2014, 89(10), 1368-1377 (Year: 2014).*
Application No. PCT/US 21/29316, International Search Report and Written Opinion dated Aug. 9, 2021.

* cited by examiner

*Primary Examiner* — Yevgeny Valenrod
(74) *Attorney, Agent, or Firm* — Galvin Patent Law LLC; Brian R. Galvin

(57) ABSTRACT

The invention provides methods for reducing the percentage of body fat, increasing the level of adiponectin, and/or treating or reducing the risk of cardiovascular disease (CVD) and coronary heart disease (CHD). Such methods include administering to an animal or human sufficient levels of a compound comprising a tri blend of HPMC (K15, K100, and K200) and myristic fatty acid.

17 Claims, 3 Drawing Sheets

METHOD FOR INCREASING SERUM ADIPONECTIN FOR TREATMENT AND REDUCTION OF THE RISK OF CARDIOVASCULAR, VASCULAR, AND RELATED DISEASES

CROSS-REFERENCE TO RELATED APPLICATIONS

The present application is a continuation application and relies on the disclosures of and claims priority to and the benefit of the filing dates of U.S. application Ser. No. 16/118,340 filed Aug. 30, 2018 and U.S. Provisional Application No. 62/552,378, filed Aug. 30, 2017. The disclosures of those applications are hereby incorporated by reference herein in their entireties.

BACKGROUND

Field of the Invention

The field of invention relates to the use of a composition comprising a blend of HPMC (Hydroxypropyl Methyl Cellulose) and an anti-inflammatory myristic fatty acid for use in increasing serum adiponectin and reducing the risk of cardiovascular disease. The composition of the present invention increases plasma levels of the hormone adiponectin which is correlative to reducing the risk of cardiovascular disease (CVD).

Further, the field of the invention relates to the use of a composition comprising a high specific blend of HPMC (Hydroxypropyl Methyl Cellulose) and an anti-inflammatory myristic fatty acid for use in increasing serum adiponectin and reducing the percentage of body fat. The composition of the present invention increases plasma levels of the hormone adiponectin, which is correlative to a decrease in obesity and/or excessive visceral body fat accumulation.

Specifically, the present invention is directed to compositions comprising HPMC and an anti-inflammatory, such as myristic acid, for the purpose of increasing plasma adiponectin and reducing the percentage of body fat.

DESCRIPTION OF RELATED ART

With the exception of the subject invention, measurements and methods to increase adiponectin by using treatments that increase its plasma levels are rare and have been shown to be ineffective. Current pharmacological fat loss treatment regimens generally have negative side effects and are either unable to increase adiponectin or they are ineffective at burning fat.

The following patents, published patent applications, and non-patent literature are incorporated herein by reference.

There have been patents issued covering HPMC to lower serum cholesterol levels, however those patents (e.g., U.S. Pat. Nos. 5,585,366 and 5,721,221) do not provide treatments for increasing adiponectin. Other references include:

U.S. Pat. No. 8,936,817 teaches a preparation for weight loss management.

WO 2002072149 A1 teaches methods for reducing fat by administration of adiponectin.

U.S. Patent Publication No. 20120009165 teaches blood-adiponectin-concentration increase-accelerator and/or decrease-inhibitor thereof.

U.S. Pat. No. 8,883,138 teaches an adiponectin production accelerating composition.

U.S. Patent Publication No. 20090088462 teaches a pharmaceutical composition for enhancing adiponectin.

BioMed Research International published non-patent literature; New insight into adiponectin role in obesity and obesity-related. BioMed Research International Volume 2014, Article ID 658913, 14 pages; Ersilia Nigro, Olga Scudiero, Maria Ludovica Monaco, Alessia Palmieri, Gennaro Mazzarella, Ciro Costagliola, Andrea Bianco, and Aurora Daniele, published 7 Jul. 2014.

University of Toronto Medical Journal published non-patent literature; Leptin and adiponectin: Examining their clinical significance in obesity. Joelle Tan, MBBS Candidate, Monash University, Melbourne, Australia William T. Gibson, MD, PhD, FRCPC, FCCMG, Associate Professor, Department of Medical Genetics, University of British Columbia, Senior Clinician Scientist, Child and Family Research Institute, Published in UTMJ, Volume 92, Number 2, March 2015.

Diabetes Journal published non-patent literature; Discrimination between obesity and insulin resistance in the relationship with adiponectin, Fahim Abbasi, James W. Chu, Cindy Lamendola, Tracey McLaughlin, John Hayden, Gerald M. Reaven, Peter D. Reaven, published in Diabetes, Volume. 53, March 2004.

Reviews in Endocrine and Metabolic Disorders published non-patent literature; Adiponectin and energy homeostasis, Bonggi Lee and Jianhua Shao, Department of Pediatrics, University of California San Diego, La Jolla, Calif. 92093, published in final edited form as: Rev. Endocr. Metab. Disord. 2014 June; 15(2): 149-156.

Adiponectin and energy homeostasis published non-patent literature; Adiponectin oligomers as potential indicators of adipose tissue improvement in obese subjects, Anna De Rosa, Maria Ludovica Monaco, Mario Capasso, Pietro Forestieri, Vincenzo Pilone, Carmela Nardelli, Pasqualina Buono and Aurora Daniele, published in European Journal of Endocrinology (2013) 169 37-43.

The Journal of Biological Chemistry published non-patent literature; Structure-function studies of the adipocyte-secreted hormone Acrp30/adiponectin: Implications for metabolic regulation and bioactivity, Pajvani U B, Du X, Combs T P, Berg A H, Rajala M W, Schulthess T, Engel J, Brownlee M, Scherer P E., published in J. Biol. Chem. 2003 Mar. 14; 278(11): 9073-85.

The European Journal of Clinical Nutrition Factors published non-patent literature; Factors determining the risk of the metabolic syndrome: is there a central role for adiponectin? Calton E K, Miller V S, Soares M J, published in Eur. J. Clin. Nutr. 2013 May; 67(5): 485-91.

Annals of Nutrition and Metabolism published non-patent literature; Molecular analysis of the adiponectin gene in severely obese patients from Southern Italy, A Daniele, R. Cammarata, F. Pasanisi, C. Pinelli, G. Salvatori, G. Calcagno, R. Bracale, G. Labruna, C. Nardelli, P. Buono, L. Sacchetti, F. Contaldo, G. Oriani, published in Annals of Nutrition and Metabolism, November 2008.

International Journal of Hypertension published non-patent literature; Chronic kidney disease, obesity and hypertension: the role of leptin and adiponectin, M. Tesauro, A Mascali, O. Franzese, S. Cipriani, C. Cardillo, and N. Di Daniele, published in International Journal of Hypertension Volume 2012.

Please also see "References" section at end of current specification below, directly before "Claims" section.

SUMMARY

The present invention provides patients with a method which increases adiponectin thereby protecting against cardio-vascular disease (CVD), stroke, heart attack and atherosclerosis.

An objective of the present invention is to provide patients with an increase in adiponectin and a corresponding decrease in cardiovascular and vascular disease. The invention is also to a product that can be safely, effectively and easily taken on a daily basis.

The prevalence of heart disease and cardiovascular disease (CVD) continues to be the leading cause of death for men and women according to the Centers for Disease Control and Prevention. Approximately 647,000 Americans die from heart disease each year. Also, according to the CDC, about 805,000 Americans have heart attacks each year. Low levels of serum adiponectin have clinically been shown to be correlative to cardiovascular disease. The present invention safely increases adiponectin through a highly tolerable method. Additionally, this application teaches and includes clinical evidence that the claimed composition and method safely and effectively increases adiponectin and correlatively reduces the risk of CVD.

In addition, according to the American Heart Association as quoted in Science Daily, in 2016 the number of all adults in the United States classified as having some type of CVD is 24.3 million. This number does not include people with high blood pressure. Once you reclassify this category to include all those persons with high blood pressure, the number increases to 121.5 million persons having some type of cardiovascular disease (CVD).

In one embodiment of the present invention, a method is provided whereby a composition including HPMC and an anti-inflammatory, such as myristic acid, is used to increase blood levels of adiponectin. This composition is a safe, easy to take, and highly effective therapy to treat cardiovascular disorders including coronary heart disease (CHD) and stroke.

A number of clinical studies have significantly demonstrated decreased adiponectin to be an independent risk factor for cardiovascular disease. Conversely, increased adiponectin has a favorable effect on cardiovascular heart disease, atherosclerosis and vascular health. Increased or higher levels of adiponectin plays a role in the protection and inhibition of vascular disease. Also, numerous clinicals have shown lower levels of adiponectin are significantly more susceptible to increasing vascular disorders and cardiovascular disease (CVD).

Numerous studies have identified adiponectin deficiency as an independent risk factor for coronary heart disease, heart attacks, strokes and other cardiovascular complications. Conversely, higher levels of adiponectin can alleviate vascular dysfunctions and have vascular protective effects.

In a double-blind placebo controlled randomized university clinical trial, embodiments of the present invention showed significant efficacy in the area of effectively increasing adiponectin. The invention comprises food grade ingredients that are generally recognized as safe (GRAS). Myristic acid is also safe. The clinical also reported increased levels of serum adiponectin which were superior to other treatments.

The objective of the present invention is to provide patients with an increase in adiponectin and a decrease in percentage of body fat. In a preferred embodiment, the invention is a product that can be safely, effectively, and easily taken on a daily basis. In another embodiment of the present invention, a method is provided whereby a composition including HPMC and/or anti-inflammatory, such as a myristic fatty acid, is used to reduce a human's percentage of body fat.

Embodiments of compositions and methods described herein to provide patients with an increase in adiponectin and/or a decrease in percentage of body fat, body mass, waist circumference, and other indicators of successful treatment and prevention of obesity.

One embodiment of the composition is a product that can be safely, effectively, and easily taken on a daily basis.

The prevalence of obesity and accumulation of visceral fat has reached alarming rates in the United States and abroad. The Center for Disease Control reported that 66% of adults in the United States for the period 2003 to 2004 were overweight or obese. The trends are moving in an unfortunate direction, with adults who are overweight and obese increasing to 71% for the period 2013 to 2014. The primary concerns regarding excess body fat accumulation and obesity are the increased risks in a number of comorbidities, including type 2 diabetes, hypertension, and cardiovascular disease.

There is great interest and importance in reducing adiposity in overweight and obese individuals. Plasma adiponectin is correlative to obesity and the accumulation of visceral fat. The present invention increases adiponectin through a highly tolerable method. Additionally, this application teaches and includes clinical evidence that the claimed composition and method increases adiponectin and correlatively decreases the percentage of body fat.

In one embodiment of the present invention, a method is provided whereby a composition including HPMC and/or an anti-inflammatory, such as a myristic fatty acid, is used to increase blood levels of adiponectin. An increase in adiponectin has been correlated to the improvement of energy metabolism, obesity, and excessive stored fat related diseases, such as diabetes, cardiovascular disease, inflammatory related diseases, hypertension, chronic kidney disease (CKD) and several types of cancer.

In another embodiment of the present invention, a method is provided whereby a composition including HPMC and/or an anti-inflammatory, such as a myristic fatty acid, is used to reduce an animal's, including a human's, percentage of body fat.

In a double-blind placebo controlled randomized university clinical trial, embodiments of the present invention showed significant efficacy in the area of waist circumference reduction, percentage of body fat reduction, and weight loss. The invention comprises a food grade ingredient that is generally recognized as safe (GRAS). Myristic acid is also safe. The clinical study also reported anthropometric efficacy responses which were superior to other treatments.

Aspect 1 is a method of increasing the level of adiponectin in the plasma or bloodstream, comprising administering a daily dose to a patient of a composition comprising HPMC and myristic fatty acid.

Aspect 2 is a method of Aspect 1, wherein the method reduces the percentage of body fat.

Aspect 3 is a method of Aspect 1 whereby the daily dose of HPMC and myristic fatty acid is administered for a period of time from 4 weeks to 8 weeks.

Aspect 4 is a method of Aspect 1 whereby the daily dose of HPMC and myristic fatty acid is administered for a period of time from 4 weeks to 8 weeks, whereby said daily dose comprises about 0.50 to about 10.00 grams.

Aspect 5 is a method of Aspect 1, whereby the method increases the level of adiponectin in the plasma or bloodstream by around 40 to 60 percent after around 4 weeks of treatment.

Aspect 6 is a method of Aspect 1, whereby the method increases the level of adiponectin in the plasma or bloodstream by around 100 to 125 percent after around 8 weeks of treatment.

Aspect 7 is a method of Aspect 1, whereby a formulation of the composition has a minimum viscosity of about 25,000 cps.

Aspect 8 is a method of Aspect 1, whereby the composition is consumed with a drink, shake, or mixed with any other food.

Aspect 9 is a method of Aspect 1, whereby the method reduces the percentage of body fat by around 1 to 10 percent after 4 weeks of treatment.

Aspect 10 is a method of Aspect 1, whereby the method reduces the percentage of body fat by around 10 to 20 percent after 8 weeks of treatment.

Aspect 11 is a composition for increasing the level of adiponectin in the plasma or bloodstream comprising HPMC and myristic fatty acid.

Aspect 12 is a composition of Aspect 11, whereby the percentage of HPMC in the composition is around 98% and the myristic fatty acid in the composition is around 2%.

Aspect 13 is a composition of Aspect 11, whereby the composition is administered in powder form.

Aspect 14 is a composition of Aspect 11, whereby the composition is administered in powder form mixed in foodstuff or beverages.

Aspect 15 is a composition of Aspect 11, whereby the composition is administered in capsule form.

Aspect 16 is a composition of Aspect 11, whereby the composition is administered in tablet form.

Aspect 17 is the tri blended formula of Aspect 13 whereby the HPMC level is equal to or greater than the average viscosity level of around 25,000 cps.

Aspect 18 is the tri blended formula of Aspect 13 whereby the HPMC level is equal to or less than the average viscosity level of around 75,000 cps.

Aspect 19 is the tri blended formula of Aspect 13 that is formulated for timed release in the digestive tract of a human or animal.

Aspect 20 is the tri blended formula of Aspect 25 whereby K15 is released more rapidly than K200.

Aspect 21 is a composition of Aspect 11, whereby the weight percentage of HPMC in the composition is about 98 weight percent and the weight percent of myristic fatty acid in the composition is around 2 weight percent.

Aspect 22 is the tri blended formula of Aspect 13 wherein the formula contains about 20 to about 60 weight percent K100.

Aspect 23 is the tri blended formula of Aspect 13 wherein the formula contains about 5 to about 25 weight percent K200.

BRIEF DESCRIPTION OF THE DRAWINGS

The accompanying drawings illustrate certain aspects of embodiments of the present invention and should not be used to limit the invention. Together with the written description the drawings explain certain principles of the invention.

DETAILED DESCRIPTION

Figure 1:
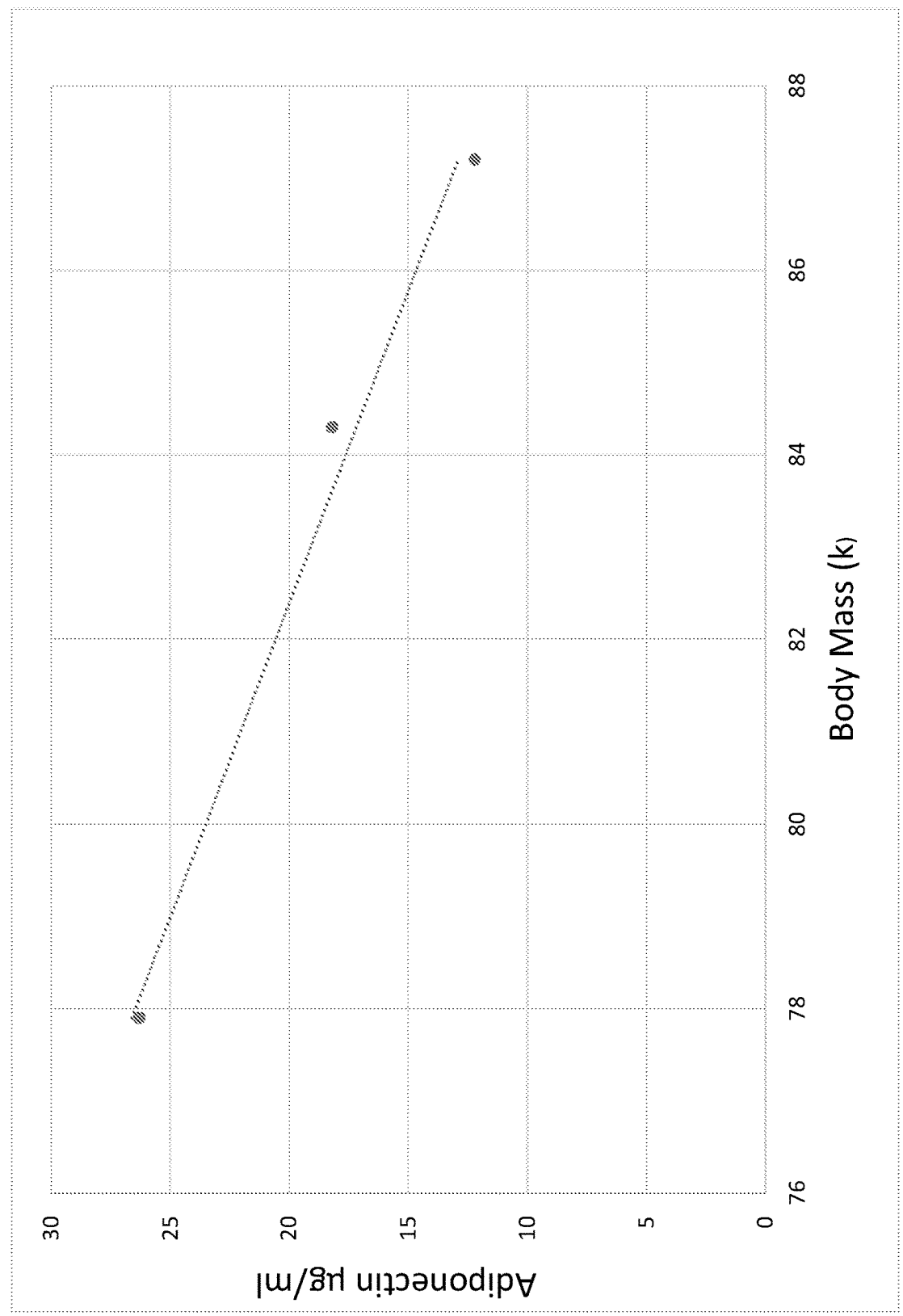
FIG. 1 is a graphical depiction illustrating the correlative relationship between body mass and plasma adiponectin levels.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary or explanatory in nature and, thus, variations that do not depart from the essence of the invention are intended to be within the scope of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Low serum adiponectin levels have been identified as a key factor involved in regulating visceral fat accumulation and obesity. In one preferred embodiment, the invention herein comprises a tri blend of high viscosity HPMC with the blend averaging in the range of about 25,000 cps, although the HPMC blend can range from around 5,000 cps to 75,000 cps, such as from 5,000 cps to 10,000 cps, 10,000 cps to 15,000 cps, and so on. The anti-inflammatory ingredient comprising myristic fatty acid, in a preferred embodiment, averages around 2% to 10% of the overall composition, but can range from 0.1% to 10%, such as from 0.1% to 0.2%, from 0.2% to 0.3%, and so on.

Low serum adiponectin levels have also been identified as a factor associated with the risk of coronary heart disease (CHD) and cardiovascular disease (CVD). In one preferred embodiment, the invention herein comprises a tri blend of high viscosity HPMC with the blend averaging in the range from around 5,000 cps to 75,000 cps, such as from 5,000 cps to 10,000 cps, 10,000 cps to 15,000 cps, and so on. The anti-inflammatory ingredient comprising myristic fatty acid, in a preferred embodiment provides 0.5 mg to 500 mg myristic fatty acid to the human per day.

A key attribute of the efficacy in terms of raising adiponectin with no or limited side effects was the dual challenge solved by the invention. Raising adiponectin has numerous positive and health protective qualities, including curbing obesity, reducing fat and fat accumulation, as well as alleviating inflammation, diabetes, and cardiovascular disease. Therefore, inventing a therapeutic composition to safely raise adiponectin would be beneficial in terms of preservation or treatment of these and other obesity related conditions, but doing so safely and effectively in the way achieved by the present invention is not taught by the prior art.

The invention also provides a composition for effectively and safely reducing the percentage of body fat in animals, such as humans, and correspondingly increasing the plasma level of adiponectin by administering the composition over a minimum of, in one aspect, a 4- to 8-week period of time to both increase adiponectin and reduce the percentage of body fat. The period of administration may be administered at a minimum of from 1 week to 20 weeks, such as from 1 week to 2 weeks, 2 weeks to 3 weeks, and so on. In a preferred embodiment, the period of administration is at least 4 to 8 weeks. The period of administration may also be a few days, and the treatment may occur over the lifetime of a treated individual.

Also, raising adiponectin has numerous positive and health protective qualities, including for cardiovascular disease. Therefore, a therapeutic composition to safely raise adiponectin would be beneficial in terms of a treatment of cardiovascular disease (CVD) or coronary heart disease (CHD). Evidence of clinical studies indicates that adiponectin deficiency is an independent risk factor for cardiovascular disease. Coronary heart disease, heart attacks, strokes and other cardiovascular complications have been shown to be ameliorated by increasing adiponectin. The composition described herein has been demonstrated as a safe and effective way to significantly elevate adiponectin levels to reduce the risk of cardiovascular disease (CVD) and coronary heart disease (CHD).

Experimental results of this non-pharmacological and highly tolerable approach, according to a clinically studied formula, show surprising and unexpected superiority over what is practiced by the prior art. The invention provides a composition for effectively and safely reducing the risk of cardiovascular (CVD) in animals and humans. In particular embodiments, the period of administration may be administered at a minimum of 8 to 20 weeks. In a preferred embodiment, the period of administration is at least 8 weeks. The period of administration may also be a few days, and the treatment may occur safely over the lifetime of a treated individual.

Experimental results of this non-pharmacological and highly tolerable approach, according to a clinically studied formula, show surprising and unexpected superiority over what is practiced by the prior art. One preferred formula reported clinical results of increasing adiponectin by around 115%.

Prior to subjecting a preferred formula to clinical testing at a renowned university there were multiple iterations of the formula. Despite obtaining knowledge through the fine tuning and guidance of the invention, the ultimate level of significant efficacy results achieved in a clinical setting was surprising and unexpected.

Twenty-two women completed an 8-week placebo controlled, double-blind study. Results reflecting an increase in adiponectin are shown in Table 1.

TABLE 1

| Adiponectin (µg/ml) | Week 0 | Week 4 | Week 8 |
|---|---|---|---|
| Invention | 12.2 ± 2.4 | 18.2 ± 2.6 | 26.3 ± 3.0 |

Serum adiponectin levels were significantly increased ($P<0.05$).

Again, the dual objective in the invention is to significantly, effectively, and safely increase adiponectin levels. A variety of fibers were included in an original rendition of possible formulas to accomplish the objective ultimately achieved by the current invention. Such fibers as glucomannan, beta glucan, guar gum and concentrated carrot fiber were employed as trial-and-error encapsulated formulas for the objective of determining in a clinical study which formula would significantly raise adiponectin. If a well-designed and university tested clinical study showed positive results in increasing adiponectin with no reported side effects, the invention could healthfully reduce the risk of coronary heart disease (CHD) and cardiovascular disease (CVD). However, it was unpredictable which combination of ingredients would be most effective and safe. The invention claimed herein, after trying different combinations and variations based on the prior art, would not have been expected by one of ordinary skill in the art to be as effective and safe as reported in the clinical.

Studies have shown a strong relationship between plasma adiponectin levels and the ability of adiponectin to protect against cardiovascular disease (CVD) and coronary heart disease (CHD).

In aspects, the invention can be consumed from encapsulated products, tablets, and can be mixed into foods, shakes, flavored drink mixes, juices, yogurt, health bars, pastries, cereals, oatmeal, eggs and flavored water or soups.

Regarding the university study specifically, the preferred formula which was subjected to clinical testing in a university setting was approved by the University's Institutional Review Board (IRB), including blood collection and biochemical analysis. The serum adiponectin was determined using an enzyme immunoassay. The university certified that all applicable institutional and government regulations concerning the ethical use of human volunteers were followed.

The present invention has shown in a published clinical study to be effective at raising plasma adiponectin concentrations. In one aspect, the invention may be taken in the form of an encapsulated product or may be consumed with any hot beverage, soup, or any liquid as stirred, shaken, or otherwise fully or partially dissolved. However, the invention may be administered by any acceptable means of administering a composition.

According to this study, the invention provides a method of significantly increasing plasma adiponectin levels in humans for a time of around 8 weeks, although the time of administering the composition may be shorter or longer. With daily consumption of around 2.4 grams of the composition taught by the current invention, the level of adiponectin in the blood generally changes at around four weeks, and more so at eight weeks.

The invention, in one aspect, may be consumed daily on an indefinite basis as the invention is safe and well tolerated. The invention is preferably mixed in any liquid, such as shake or food form, including food (e.g., oatmeal), a beverage or bars.

A clinical study was conducted at the University of Connecticut measuring the influence the invention had on plasma adiponectin levels. The subjects completed an 8-week placebo controlled, double blind study. Serum adiponectin was assessed at pre-, mid-, and post-intervention. Significant increases occurred in serum adiponectin levels over the mid- and post-intervention.

(Response of Serum Adiponectin)

|  | Week 0 | Week 4 | Week 8 |
|---|---|---|---|
| Adiponectin Plasma Levels (µg/ml) | 12.2 ± 2.4 | 18.2 ± 2.6 | 26.3 ± 3.0 |

There is a direct and inverse relationship between the increase of plasma adiponectin and the capability of adiponectin to protect against cardiovascular disease (CVD), vascular disease and coronary heart disease (CHD). Consistent with clinical studies and clinical observations it has been shown that adiponectin deficient humans are more susceptible to developing vascular disorders and cardiovascular diseases. Additionally, increasing adiponectin exerts multiple protective effects on the vascular system, including cardiovascular disease (CVD) and coronary heart disease (CHD). Clinical observations have shown a high correlative relationship between adiponectin levels and cardiovascular disease. Also, circulatory levels of serum adiponectin have shown an inverse relationship to the risk of cardiovascular events such as strokes and heart attacks. Clinical studies have demonstrated a positive connection between higher levels of adiponectin promoting atherosclerotic and vascular repair. A safe and effective means to treat these diseases by increasing adiponectin could be useful as a therapy for the prevention and treatment of vascular diseases. This invention hence may be useful as a therapy to effectively and safely increase adiponectin.

Experimental results of this non-pharmacological and highly tolerable approach, according to a clinically studied formula, show surprising and unexpected superiority over what is practiced by the prior art. One preferred formula reported clinical results of body fat reduction of around 11% with the percentage of body fat being reduced from 43.4% down to 36.1% in 8 weeks.

Prior to subjecting a preferred formula to clinical testing at the University of Connecticut there were multiple iterations of the formula. After developing numerous fiber related formulas which had limited impact on losing weight or reduction of waist circumference, a non-choleric fiber containing 15K HPMC was tested, which appeared to work for losing weight. The formula was advanced to 200K of HPMC in capsule form, and projecting this higher viscosity level had an impact on losing weight and fat more effectively. However, the 200K HPMC formula carried with it unacceptable side effects, including, but not limited to, stomach and intestinal cramping, constipation, and intestinal pain. A formula using HPMC providing for efficacy of fat loss, no side effects and, most importantly, substantively increasing adiponectin, was continually modified. The formulation of a tri blend was developed in which Kl 5, Kl 00, and K200 was used. The results of the tri blend HPMC formula seemed to work on a sample basis, eventually leading to a formula used to measure adiponectin levels in a university developed clinical study.

There were numerous ingredients used originally prior to the preferred formula being subjected to a randomized, double blinded, placebo controlled, university clinical study. The various formulas were blended and encapsulated and provided to approximately 4 network marketing companies for efficacy feedback to formulate the best formula to be used in a clinical trial.

Despite obtaining knowledge through the fine tuning and guidance of the invention, the ultimate level of significant efficacy results achieved in a clinical setting was surprising and unexpected to one of ordinary skill in the art.

Twenty-two women completed an 8-week placebo controlled, double-blind study. Results from the study are shown in Tables 1-4.

TABLE 1

| Body Mass | Week 0 | Week 4 | Week 8 |
|---|---|---|---|
| Clinical Formula | 87.2 ± 6.2 | 84.3 ± 5.1 | 77.9 ± 5.1 |
| Placebo | 86.9 ± 7.2 | 85.1 ± 5.1 | 82.7 ± 3.8 |

Significant decreases (P<0.05) were observed for body weight.

TABLE 2

| Body Fat (%) | Week 0 | Week 4 | Week 8 |
|---|---|---|---|
| Clinical Formula | 43.44 ± 4.1 | 39.9 ± 3.3 | 36.1 ± 3.6 |
| Placebo | 44.30 ± 2.0 | 41.9 ± 1.7 | 40.9 ± 1.2 |

The percentage of body fat reduction achieved significant results (P<0.05).

TABLE 3

| Circumference Waist | Week 0 | Week 4 | Week 8 |
|---|---|---|---|
| Clinical Formula | 101.9 ± 4.4 | 96.5 ± 3.7 | 92.1 ± 3.9 |
| Placebo | 102.5 ± 3.6 | 99.2 ± 4.0 | 97.4 ± 4.0 |

Waist circumference showed a significantly greater (P<0.05) reduction from baseline measurement.

TABLE 4

| Adiponectin (µg/ml) | Week 0 | Week 4 | Week 8 |
|---|---|---|---|
| Clinical Formula | 12.2 ± 2.4 | 18.2 ± 2.6 | 26.3 ± 3.0 |
| Placebo | 12.6 ± 2.0 | 19.3 ± 3.3 | 21.8 ± 3.1 |

Serum adiponectin levels were significantly increased (P<0.05). The objective of the invention is to increase adiponectin levels and to correspondingly reduce the percentage of stored body fat. It is known that the consumption of fibers, including dietary fiber, provides positive metabolic effects, such as reduction in glucose and insulin concentrations. The effects of various fibers on adiponectin, body composition, fuel utilization, and excessive fat accumulation had not been previously widely studied or known. A variety of fibers were included in an original rendition of possible formulas to accomplish the objective ultimately achieved by the current invention. Such fibers as glucomannan, beta glucan, guar gum and concentrated carrot fiber were employed as trial-and-error encapsulated formulas for the objective of determining in a clinical study which formula would raise adiponectin and correlatively lower body fat. If a well-designed and university tested clinical study showed positive results in increasing adiponectin and reducing body fat, with no reported side effects, the invention could healthfully reduce the global pandemic of obesity and the increased risk of a number of comorbidities including hypertension, type 2 diabetes and coronary heart disease. However, it was unpredictable which combination of ingredients would be most effective and safe. The invention claimed herein, after trying different combinations and variations based on the prior art, would not have been expected by one of ordinary skill in the art to be as effective and safe as it was, especially based on data known before such experimentation.

Upon the completion of the clinical study and obtaining the independent results, achievement of the two objectives was met:

1. The significant increase in plasma adiponectin; and
2. The significant reduction in the percentage of body fat.

The invention can be easily consumed from encapsulated products, tablets, and can be mixed into foods, shakes, flavored drink mixes, juices, yogurt, health bars, pastries, cereals, oatmeal, eggs and flavored water or soups.

The formulations produced for feedback prior to subjecting to a clinical study included, but were not limited to, the following formulas and percentage of respective compositions. Weight loss, speed of weight loss, and waist circumference were the three chosen and most critical feedback criteria.

| Formula 1 | |
|---|---|
| Ingredient | Percentage of Formula (w/w) |
| Carrot Powder | 25% |
| Glucomannan | 20% |
| Beta Glucan | 30% |
| HPMC (15K) | 25% |
| Total | 100% |

| Formula 2 | |
|---|---|
| Ingredient | Percentage of Formula (w/w) |
| Carrot Powder | 25% |
| Glucomannan | 30% |
| HPMC (15K) | 30% |
| Guar Gum | 15% |
| Total | 100% |

| Formula 3 | |
|---|---|
| Ingredient | Percentage of Formula (w/w) |
| HPMC (K15) | 40% |
| HPMC (K100) | 20% |
| Beta Glucan | 20% |
| Carrot Powder | 20% |
| Total | 100% |

| Formula 4 | |
|---|---|
| Ingredient | Percentage of Formula (w/w) |
| HPMC (K100) | 90% |
| Myristic Fatty Acid | 10% |
| Total | 100% |

| Formula 5 | |
|---|---|
| Ingredient | Percentage of Formula (w/w) |
| Carrot Powder | 30% |
| HPMC (Blend K15 and K100) | 60% |
| Myristic Acid | 10% |
| Total | 100% |

| Formula 6 | |
|---|---|
| Ingredient | Percentage of Formula (w/w) |
| HPMC Tri blend (K15, K100, K200) | 90% |
| Myristic Fatty Acid | 10% |
| Total | 100% |

Based on the clinical testing and trial-and-error, the tri blend was chosen for its promising time dependent digestive response.

Clinically Tested Formula (Formula Selected)

| Ingredient | Percentage of Formula (w/w) |
|---|---|
| HPMC Tri blend (K15, K100, and K200) | 98% |
| Myristic Fatty Acid | 2% |
| Total | 100% |

Also, according to testing, a tri blend averaging a viscosity measurement of around 25,000 cps was ultimately chosen for the university clinical trial.

Surprisingly, this formula used in the clinical study reported a substantive increase in adiponectin. The formula was shown to be a useful therapeutic approach against obesity and obesity related diseases.

The tri blend nomenclature represents three different forms of HPMC, each with a different viscosity. The final formula used included 2% of myristic acid. A formula or oral composition may comprise from about 1 to about 10 weight percent of myristic acid.

This same formula produced the most surprising results of a significant increase in adiponectin and its increase correlating near perfectly with—% of body fat, waist circumference and weight loss. Results demonstrated this invention is a novel and safe therapy for increasing adiponectin and the unique treatment of obesity, excess fat accumulation and obesity-related diseases.

During testing, the high viscosity form of HPMC (K200) caused painful side effects to such an extent that the project of using HPMC was nearly abandoned. The modification of HPMC usage and the development of the tri blend resolved side effect issues of painful stomach and intestinal cramping. It was the unique and synergistic attributes of the formula which were the cause of efficacy in terms of significantly increasing adiponectin and the fact that there were no side effects reported in the study. The efficacy results reported in the clinical trial were substantive and superior to the most optimistic results expected. The tri blend formula was novel in every respect—including use of any of the ingredients used to increase adiponectin.

Turning to the figures, FIG. 1 graphically illustrates the correlative relationship between body mass and plasma adiponectin levels. The coefficient of determination ($r^2$) being a strong and highly correlative number of 0.984.

Figure 2:
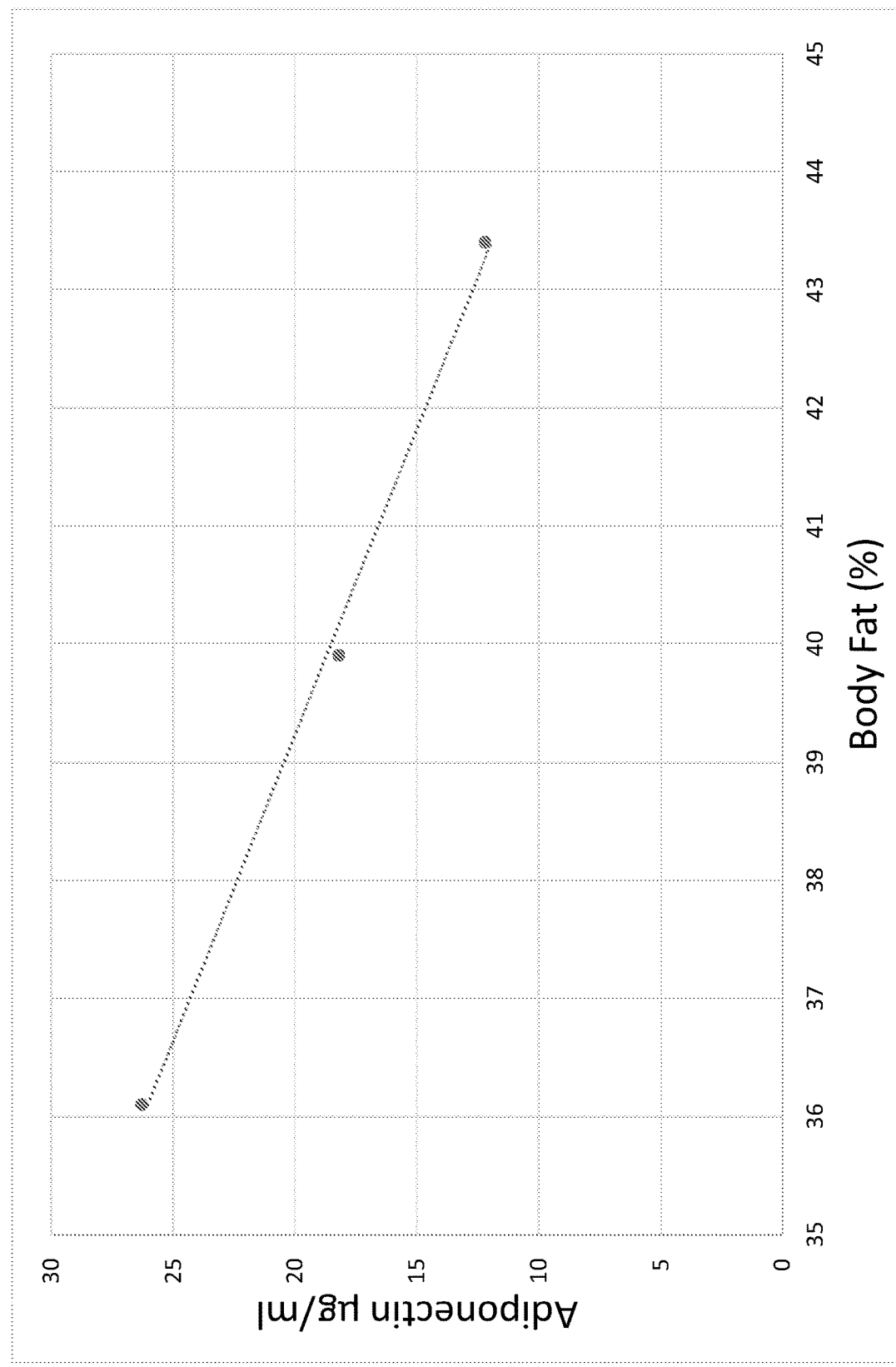
FIG. 2 is a graphical depiction illustrating the initial relationship between plasma adiponectin and the percentage of body fat. As illustrated, there is a negative correlation between the decrease in the percentage of body fat and the concentration of adiponectin in the plasma reflecting that higher adiponectin levels are correlative to lower body fat.

FIG. 2 graphically illustrates the strong relationship between plasma adiponectin and the percentage of body fat; indicating that higher plasma adiponectin is directly correlative with lower body fat. The coefficient of determination ($r^2$) was a near perfect 0.996.

Figure 3:
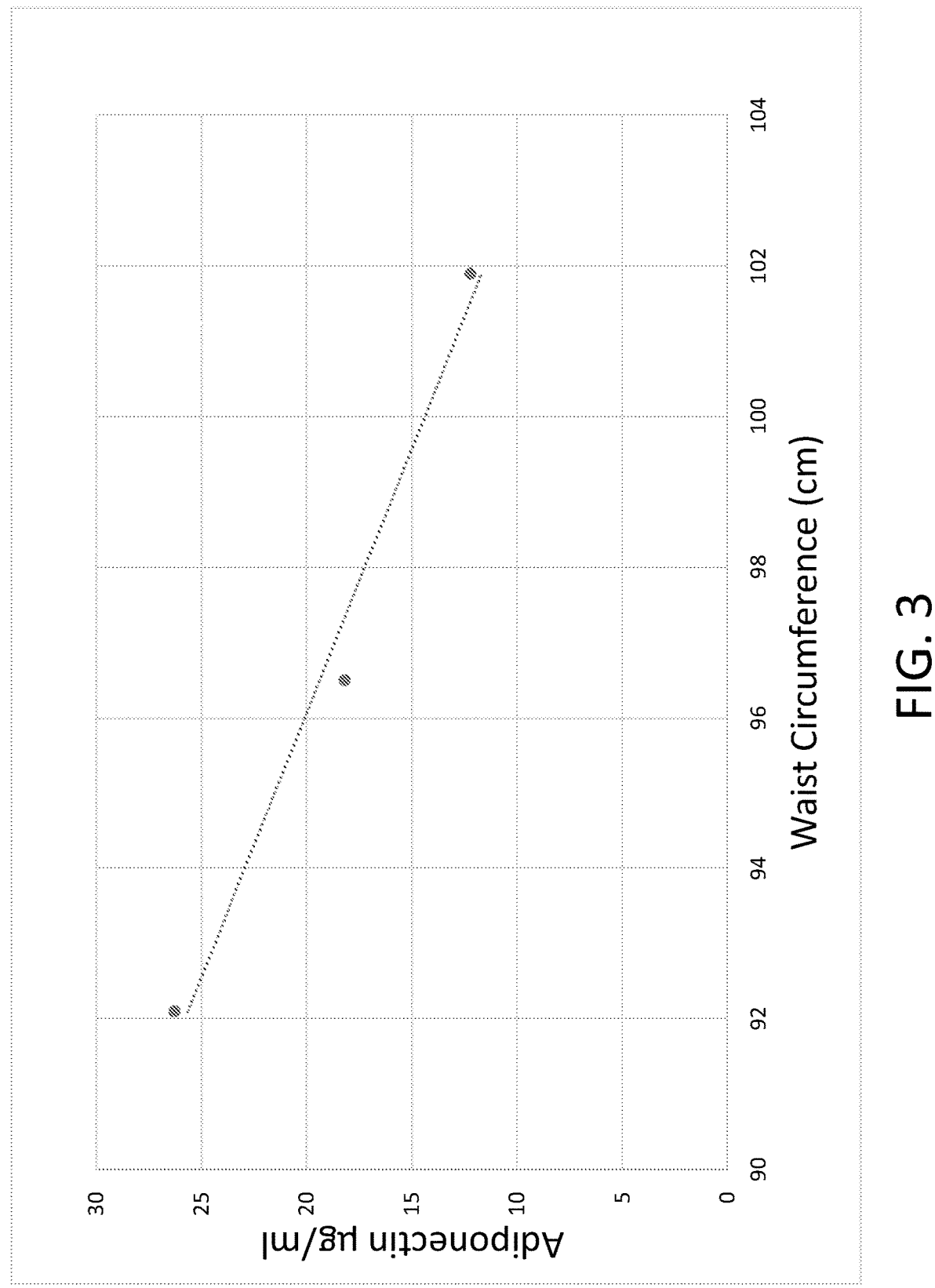
FIG. 3 is a graphical depiction illustrating the strong relationship and negative correlation between plasma adiponectin levels and the waist circumference, indicating that as adiponectin increases the waist circumference decreases.

FIG. 3 graphically illustrates the strong relationship between plasma adiponectin levels and the circumference of the waist. As illustrated, there is a strong negative correlative relationship between waist circumference and plasma level of adiponectin, indicating that as adiponectin increases the waist circumference decreases with the coefficient of determination ($r^2$) being 0.979.

Regarding the University of Connecticut study specifically, the preferred formula which was subjected to clinical testing in a university setting was approved by the University's Institutional Review Board (IRB), including blood collection and biochemical analysis. The serum adiponectin was determined using an enzyme immunoassay. The university certified that all applicable institutional and government regulations concerning the ethical use of human volunteers were followed.

The level of the strength of the correlative relationship between adiponectin and the other key variables as shown in FIGS. 1, 2, and 3 were unexpected. The surprisingly strong coefficient of determination ($r^2$) is further evidence of the correlative properties with adiponectin and the other three variables.

The results of the data sets of a clinical study in which adiponectin and the three variables discussed all had a surprisingly high coefficient of determination ($r^2$) which showed an exceptionally strong and highly predictive correlation with adiponectin.

The three variables determining body mass, percentage of body fat, and waist circumference were measured as follows: 1) body mass was measured to the nearest 0.1 pound by using a calibrated clinical scale; 2) waist circumference was measured using a standard spring-loaded measuring tape; and 3) body composition, or percentage of body fat was obtained using dual-energy x-ray absorptiometry (DEXA) using a total body scanner.

Example 1

The present invention has shown in a published clinical study (Eur. J. Appl. Physiol., 2009 March; 105(5): 665-72, "Influences of a dietary supplement in combination with an exercise and diet regimen on adipocytokines and adiposity in women who are overweight") to be effective at decreasing body fat and raising plasma adiponectin concentrations. In one aspect, the invention may be taken in the form of an encapsulated product or may be consumed with any hot beverage, soup, or any liquid as stirred, shaken, or otherwise fully or partially dissolved. However, the invention may be administered by any acceptable means of administering a composition.

According to this study, the invention provides a method of significantly reducing body fat percentages and correlatively increasing plasma adiponectin levels in humans for a time of around 8 weeks to reduce the percentage of body fat and increase adiponectin plasma levels, although the time of administering the composition may be shorter or longer. With daily consumption of around 2.4 grams of the composition taught by the current invention, the percentage of body fat and the level of adiponectin in the blood generally change at around four weeks, and more so at eight weeks.

The invention, in one aspect, may be consumed daily on an indefinite basis as the invention is safe and well tolerated. The invention is preferably mixed in any liquid, such as shake or food form, including food (e.g., oatmeal) or a beverage.

Example 2

A clinical study was conducted at the University of Connecticut measuring the influence the invention had on plasma adiponectin levels and percentage of body fat. The subjects completed an 8-week placebo controlled, double blind study. Percentage of body fat and serum adiponectin amongst other factors were assessed at pre-, mid-, and post-intervention. Significant decreases were observed for percentage of body fat and body weight. Significant increases occurred in serum adiponectin levels over the mid- and post-intervention.

Response of Serum Adiponectin and Body Fat Percentage

|  | Week 0 | Week 4 | Week 8 |
| --- | --- | --- | --- |
| Adiponectin Plasma Levels | 12.2 | 18.2 | 26.3 |
| Body Fat (%) | 43.4 | 39.9 | 36.1 |

Example 3

There is a direct and inverse relationship between the increase of plasma adiponectin and the decrease in the percentage of body fat in week 4; with these trends continuing through week 8.

The reduction of body mass is correlated with the increase in plasma adiponectin.

Response of Serum Adiponectin and Body Mass

|  | Week 0 | Week 4 | Week 8 |
| --- | --- | --- | --- |
| Adiponectin Plasma Levels | 12.2 | 18.2 | 26.3 |
| Body Mass (kg) | 87.1 | 84.3 | 77.9 |

Example 4

Response of Serum Adiponectin and Waist Circumference

|  | Week 0 | Week 4 | Week 8 |
| --- | --- | --- | --- |
| Adiponectin Plasma Levels | 12.2 | 18.2 | 26.3 |
| Waist Circumference (cm) | 101.9 | 96.5 | 92.1 |

The decrease in waist circumference is correlated with the increase in plasma adiponectin. The trend in the reduction in waist circumference in week 4 continued through week 8.

Example 5

Response of Serum Adiponectin and Hip Measurement

|  | Week 0 | Week 4 | Week 8 |
|---|---|---|---|
| Adiponectin Plasma Levels | 12.2 | 18.2 | 26.3 |
| Hip Measurement (cm) | 117.3 | 112.3 | 109.9 |

There is a correlation in the decrease in hip measurement and the increase in adiponectin. The trend in the reduction in hip measurement in week 4 continued through week 8.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary or explanatory in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

REFERENCES

All of the references cited in this disclosure are each individually incorporated by reference herein in their entireties and as such are intended to provide an efficient way of supplementing the enabling disclosure of this invention as well as provide background detailing the level of ordinary skill in the art.

Blake, G., Ridker, P A, Novel markers of vascular wall inflammation. Circ. Res. 2001; 89: 763-771.
Cavusoglu, E. Ruwende, C., et al., Adiponectin in an independent predictor of all-cause mortality, cardiac mortality, and myocardial infarction in patients presenting with chest pain. European Heart J 2006; 27:2300-2309.
Frystyk, J. Berne, C., et al., Serum adiponectin is a predictor of coronary heart disease: a population-based 10 year follow up study in elderly men. Journal of Endocrinol Metab; 2007: 92 (2): 571-576.
Hao, G. Wi, W., Serum total adiponectin level and the risk of cardiovascular disease in general population: a meta-analysis of 17 prospective studies. Atherosclerosis 2013; 228: 29-35
Ho, D Y, Cook, N R., et al., High molecular weight and total adiponectin levels and incident symptomatic peripheral artery disease in women a prospective investigation. Circulation, 2011; 124 (21): 2303-2311.
Huijuan, Kou, Qiangsun, Z., Relationship between Adiponectin, Insulin Resistance and Atherosclerosis in non-diabetic Hypertensive Patients and Healthy Adults. Journal of the American College of Cardiology, Vol 20 Issue 16 Supplement 2017.
Huijuan, Kou, et al., Journal of the American College of Cardiology; 2018.
Kanhai, D A, Kranedonk, M E., et al., Adiponectin and incident coronary heart disease and stroke. A systematic review and meta-analysis of prospective studies. Obesity Reviews: an official journal of the International Association for the Study of Obesity. 2013; 14: 555-567.
Kiris, I, Tekin, I., et al., Inverse relationship between adiponectin levels and subclinical carotid atherosclerosis in patients undergoing coronary artery bypass grafting. International Heart. 2006; 47: 855-866.
Kizer J R., Benkeser D., Total and high molecular weight adiponectin and risk of coronary heart disease and ischemic stroke in older adults. Journal of Clinical Endocrinology Metab. 2012; 98(1):255-263.
Kollias, A., Tsiotra, P C., et al., Adiponectin levels and expression of adiponectin receptors in isolated monocytes from overweight patients with coronary artery disease. Cardiovascular Diabetol. 20112; 10 (14): 14-26.
Kumada, M, Sumitsuji, S., et al., Association of hypoadiponectinemia with coronary artery disease in men. Arteriosclerosis Thromb. Vase. Biol. 2003; 23(1): 85-89.
Liangping, Zhao, et al., The impact of serum adiponectin level on morbidity and prognosis in patients with acute myocardial infarction. Journal of the American College of Cardiology; 2017.
Libby, P, Okamoto, Y., Inflammation in atherosclerosis. Circulation Journal 2010; 74:213-220.
Margaritis, M, Antonopoulos, A S., Interactions between vascular wall and perivascular adipose tissue reveal novel roles for adiponectin in the regulation of endothelial nitric oxide synthase function in human vessels. Circulation Journal 2013; 127(22):2209-2221.
Mehrangiz, E, Somayeh, M., et al., Adiponectin as a potential biomarker of vascular disease. Vascular Health Risk Management, 2015; 11: 55-70.
Mohammadi, S., Hosseinzadeh-Attra, M J, et al., Compare the effects of different visfatin concentration on cardiovascular risk factors, adiponectin and insulin resistance in patients with T2DM., Diabetes Metab Syndrome, 2011; 5(2): 71-75.
Okui, H, Hamasaki, S., et al., Adiponectin is a better predictor of endothelial function of the coronary artery than HOMA-R, body mass index, immunoreactive insulin, or triglycerides. International Journal of Cardiology. 2008; 126:53-61.
Ouchi, N, Kobayashi, H., et al., Adiponectin stimulates angiogenesis by promoting crosstalk between AMP-activated protein kinase and Akt signaling in endothelial cells. Journal of Bio Chem, 2004; 279(2): 1304-1309.
Ouchi, N, Ohishi, M, et al., Association of hypoadiponectinemia with impaired vasoreactivity. Hypertension, 2003; 42(3):231-234.
Ouwens, D M, Cell, H., et al., The role of epicardial and perivascular adipose tissue in the pathophysiology of cardiovascular disease. Journal of Cellular Molecule. 201 O; 14(9)2223-2224.
Pischon, T, Girman, C J., et al., Plasma adiponectin levels and risk of myocardial infarction in men. JAMA. 2004; 291(14): 1730-1737, Pischon, T, Hu, F B., et al., Plasma total and high molecular weight adiponectin levels and risk of coronary heart disease in women. Atherosclerosis. 2011; 219(1):322-329.

Rothenbbacker, D., Brenner, H. et al., Adiponectin, risk of coronary heart disease and correlations with cardiovascular risk markers. 2005 European Heart Journal, Vol 26, (16) 1640-1646.

Saito, I., Yamagishi, K., et al., Total and high molecular weight adiponectin levels and risk of cardiovascular disease individuals with high blood glucose levels. Atherosclerosis, Vol. 229 Issue (1) 222-227 (2013).

Sattar, N, Wannamethee, G., et al., A prospective study and meta-analysis. Circulation, 2006; 114:623-629.

Seung, H, Quon, M, et al., Response to therapeutic Inventions. American College of Cardiology Vol. 49, No 5; 2007.

Sewon, L., Hyo, B., Role of adiponectin in metabolic and cardiovascular disease. Journal of Exercise Rehab. 2014, April; 10(2) 54-59.

Shibata, R., Sato, K., et al., Adiponectin protects against myocardial ischemia reperfusion injury through AMPK- and COX-2-dependent mechanisms. Natural Medicine. 2005; 11(10): 1096-1103.

Sook, L., Park, S S., et al., Association between adiponectin levels and coronary heart disease and mortality; a systematic review and met-analysis. International Journal of Epidemiology. 2013; 42: 1029-1039.

Suzuki, S, Wilson-Kubalek, E M, et al., The oligomeric structure of high molecular weight adiponectin. FEBS Letter. 2007; 581(5):809-814.

Tao, L., Gao, E., Adiponectin cardio-protection after myocardial ischemia/reperfusion involves the reduction of oxidative/nitrative stress. Circulation. 2007; 115(11): 1408-1416.

Tao, L., Wang, Y., et al., Adiponectin an indispensable molecule in rosiglitazone cardio-protection following myocardial infarction. Circulation Res. 2010; 106(2):409-417.

Teoh, H., Strauss, M H., et al., Adiponectin and myocardial infarction: A paradox or a paradigm? European Heart Journal, 2006; 27:2266-2268.

Torigoe, M, Matsui, H., et al., Impact of the high molecular weight form of adiponectin on endothelial function in healthy young men. Clinical Endocrinology. 2007; 67(2): 276-281.

Wang, Z V, Scherer, P E, Adiponectin, cardiovascular function and hypertension. Hypertension. 2008; 51(1):8-14.

Wannamethee, S G, et al., European Journal of Cardiovascular Prevention. 201118(1):65-71.

Welsh, P, Whincup, P., Elevated adiponectin and increased risk of cardiovascular disease and mortality in asymptomatic older men: does NT-proBNP explain the paradox? Atherosclerosis. 2010; 213(1):e3.

Xu, A, Wang, Y., et al., Vascular actions of adipokines: molecular mechanisms and therapeutic implications. Advanced Pharmacol, 2010; 60:229-255.

Yamaguchi, T., Kadowaki, T., Physiological and pathophysiological roles of adiponectin and adiponectin receptors in the integrated regulation of metabolic and cardiovascular diseases. International Journal of Obesity, 2008, December; 32 S13-8 doi:10.1038.

Zampetaki, A, Kirton, J. P., et al., Vascular repair by endothelial progenitor cells. Cardiovascular Res. 2008; 78(3) 413-421.

Zhang, P, Wang, Y., et al., Overexpression of adiponectin receptors potentiates the anti-inflammatory action of sub-effective dose of globular adiponectin in vascular endothelial cells. Arteriosclerosis Thromb Vasc Biol. 2009; 29(1) 67-74.

Zhi, Z, Pengfi, Z., et al., Adiponectin ameliorates angiotensin II-induced vascular endothelial damage. Cell Stressed Chaperones. 2014; 19(5):705-713.

Zhu, W, Cheng, K. K., Vascular effects of adiponectin: molecular mechanisms and potential therapeutic intervention. Clinical Science. 2008:114:361-374.

Zoccali, C., Mallamaci, F., et al., Adiponectin, metabolic risk factors, and cardiovascular events among patients with end-stage renal disease. Journal of American Soc. Nephrology 2002; 13: 134-141.

The invention claimed is:

1. A method of treating coronary heart disease in a human, the method comprising administering to the human an amount of a composition comprising Hydroxypropyl Methyl Cellulose and myristic acid, wherein the amount is effective for treating the coronary heart disease, and wherein the administering provides about 0.5 mg to about 500 mg myristic acid to the human per day.

2. The method of treating coronary heart disease in a human according to claim 1, wherein the treating the coronary heart disease in the human comprises increasing adiponectin levels in the human.

3. The method of treating coronary heart disease in a human according to claim 1, wherein the treating the coronary heart disease in the human comprises increasing adiponectin levels and correlates to reducing a risk of at least one of a stroke, heart attack, and atherosclerosis.

4. The method of treating coronary heart disease in a human according to claim 1, wherein the treating the human comprises increasing adiponectin levels in the human and protecting against one or more vascular disorder.

5. The method of treating coronary heart disease in a human according to claim 1, wherein the treating comprises increasing adiponectin levels, improving vascular health, and providing vaso-protective properties.

6. The method of treating coronary heart disease in a human according to claim 1, wherein measuring a level of adiponectin in the human is capable of at least one of monitoring, diagnosing, or evaluating vascular disease.

7. The method of treating coronary heart disease in a human according to claim 1, wherein the administering to the human the amount of the composition comprising Hydroxypropyl Methyl Cellulose and myristic acid increases adiponectin levels in the human, and wherein the increased adiponectin levels in the human are effective to at least one of treat vascular disease in the human or improve vascular health in the human.

8. The method of treating coronary heart disease in a human according to claim 1, wherein the amount of the composition comprising Hydroxypropyl Methyl Cellulose and myristic acid is administered at least once per day.

9. The method of treating coronary heart disease in a human according to claim 1, wherein the amount of the composition comprising Hydroxypropyl Methyl Cellulose and myristic acid is administered to the human over a period of at least four weeks.

10. The method of treating coronary heart disease in a human according to claim 1, wherein the amount of the composition comprising Hydroxypropyl Methyl Cellulose and myristic acid is administered to the human over a period of at least eight weeks.

11. The method of treating coronary heart disease in a human according to claim 1, wherein the composition comprising Hydroxypropyl Methyl Cellulose and myristic acid is administered to the human in an oral formulation.

12. The method of treating coronary heart disease in a human according to claim 1, wherein the composition comprising Hydroxypropyl Methyl Cellulose and myristic acid is consumed with at least one of a drink or a shake, or wherein the composition comprising Hydroxypropyl Methyl Cellulose and myristic acid is consumed mixed with one or more food.

13. The method of treating coronary heart disease in a human according to claim 1, wherein the Hydroxypropyl Methyl Cellulose comprises a blend of Hydroxypropyl Methyl Cellulose having at least three different molecular weights or viscosity levels.

14. The method of treating coronary heart disease in a human according to claim 13, wherein the blend comprises K15, K100, and K200 Hydroxypropyl Methyl Cellulose.

15. The method of treating coronary heart disease in a human according to claim 13, wherein the blend has a viscosity range between 5,000 cps and 150,000 cps.

16. The method of treating coronary heart disease in a human according to claim 1, wherein the myristic acid is present in the composition at from 0.1% to 10% w/w.

17. A method of treating or reducing a risk of coronary heart disease in a human, the method comprising:
  administering to the human an amount of a composition comprising Hydroxypropyl Methyl Cellulose and myristic acid, wherein the amount is effective to at least one of treat the coronary heart disease or reduce a risk of the coronary heart disease in the human;
  wherein the at least one of the treating of the coronary heart disease or the reducing the risk of the coronary heart disease in the human comprises increasing serum adiponectin levels in the human; and
  wherein the administering to the human the amount of the composition of Hydroxypropyl Methyl Cellulose and myristic acid provides about 0.5 mg to about 500 mg myristic acid to the human per day.

* * * * *